United States Patent [19]

Kopf et al.

[11] Patent Number: 4,613,496
[45] Date of Patent: Sep. 23, 1986

[54] PHARMACEUTICAL CAPSULES OF RIFAMPICIN WITH UNIFORM ELUTION PROPERTIES

[75] Inventors: Helmut Kopf, Rheinfelden, Switzerland; Christian Bûcher, Freiburg, Fed. Rep. of Germany

[73] Assignee: Ciba-Geigy Corporation, Ardsley, N.Y.

[21] Appl. No.: 584,185

[22] Filed: Feb. 27, 1984

[30] Foreign Application Priority Data

Mar. 7, 1983 [GB] United Kingdom ............... 8306264

[51] Int. Cl.⁴ .................... A61K 9/48; A61K 9/52; A61K 9/64
[52] U.S. Cl. ...................... 424/14; 424/16; 424/19; 424/37; 514/255
[58] Field of Search .................. 514/255; 424/19, 14, 424/16, 37

[56] References Cited

PUBLICATIONS

Daiichi Pharm K.K., Derwent Abstract No. 01067B/01 (11/21/78).
Merck Index, Merck & Co. (1976), p. 1068.
The United States Dispensatory, 27th Ed., Lippincott (1973) pp. 1020–1030.
Goodman & Gilman, The Pharmacological Basis of Therapeutics, 5th Ed., (1975) pp. 1208–1210.
Remington's Pharmaceutical Sciences, 15th Ed. (1975) p. 1124.
Martindale, The Extra Pharmacopoeia, 27th Ed. (1977) pp. 1596–1601.

*Primary Examiner*—Albert T. Meyers
*Assistant Examiner*—C. Joseph Faraci
*Attorney, Agent, or Firm*—Michael W. Glynn; Irving M. Fishman

[57] ABSTRACT

Solid pharmaceutical preparations containing Rifampicin, crystalline cellulose, sodium lauryl sulfate and a lubricant have improved elution properties.

4 Claims, No Drawings

PHARMACEUTICAL CAPSULES OF RIFAMPICIN WITH UNIFORM ELUTION PROPERTIES

The present invention concerns pharmaceutical preparations with uniform elution properties, primarily solid pharmaceutical preparations, particularly capsules, with consistently uniform and satisfactory elution properties.

Rifampicin is a semisynthetic antibiotic, which is primarily used as tuberculostatic agent. However, due to the low solubility properties of the active ingredient, the usual solid pharmaceutical preparations, particularly capsules, containing Rifampicin show poor and/or erratic elution properties, particularly in a neutral to slightly basic medium, such as is prevailing in the lower gastrointestinal medium.

In order to overcome the poor elution properties of solid pharmaceutical preparations containing Rifampicin, it has been proposed (Japanese patent disclosure No. Sho 53-133624 of Nov. 21, 1978), that with the addition or sole use of one or more than one specifically named auxiliary substance, the unsatisfactory elution properties of such pharmaceutical preparations may be overcome. It was shown, that the elution properties of capsules containing Rifampicin as active ingredient and conventional auxiliary substances for the improvement of the elution properties of solid preparations, such as sodium lauryl sulfate, a sucrose fatty acid ester, a sorbitan fatty acid ester or dioctyl sulfosuccinate, and/or ordinary pharmaceutical auxiliaries, such as fillers, e.g. lactose, D-mannit or corn starch, which auxiliary substances are normally used together with a lubricant, such as calcium stearate, or capsules containing Rifampicin together with the lubricant alone, show unsatisfactory to poor elution properties, when tested in a medium with a pH of 3 according to the rotating basket method, as described, for example, in the US Pharmacopeia, (e.g. p. 65; 19th rev. edition, 1975; Mack Publishing, Easton (Pa) USA).

On the other hand, capsules containing mixtures of Rifampicin with crystalline cellulose alone or with crystalline cellulose together with polyoxylol 40 stearate (i.e. polyethyleneglycol 40 monostearate), polysorbate 80 (i.e. polyethylenglycol 80 sorbitan monooleate), glycerol monostearate, hydroxypropyl cellulose, or hydroxypropyl methylcellulose, magnesium stearate being present as lubricant in all of these mixtures, show satisfactory elution properties, when tested in the same medium of pH 3 according to the above mentioned rotating basked test method.

It has also been found, that the elution properties of solid pharmaceutical preparations, particularly capsules, containing Rifampicin together with conventional auxiliary ingredients, as well as with the ingredients suggested in the above mentioned Japanese patent disclosure, when determined in a test medium of a pH-value of 1.5, which more closely simulates the acidic properties of the normal and healthy human stomach, do not differ significantly from each other and can be considered as being satisfactory. The ultimate elution of both types of capsules is higher than 90%; this rate is attained somewhat faster with the solid Rifampicin preparations containing the ingredients disclosed in the above Japanese patent disclosure.

As is indicated by the data presented in the latter, it is when one proceeds towards to the more neutral and even slightly basic medium, which simulates the conditions prevailing in an abnormal human stomach or in the lower intestinal tract, that more relevant differences between the two types of preparations can be expected.

While the compositions described in the above Japanese Patent disclosure show a considerable improvement of their elution properties over those of the ordinary preparations, it has now been found, that these properties are no longer satisfactory under neutral to slightly basic conditions, e.g. in a medium of a pH-value of 7.5, particularly, when the elution rates are determined with a test method, which more accurately reflects the actual physiological conditions prevailing in the human body, than the rotating basket method.

The column dissolution rate testing method, as described, for example, by Langenbucher and Rettig, Drug Development and Industrial Pharmacy, Vol. 3(3), p. 241 (1977), has been recognized in reviews, e.g. Wagner, Biopharmaceutics and Relevant Pharmacokinetics (1971, Drug Inter Publications, Hamilton (Ill USA), and Groves and Alkan, Manuf. Chem. Aerosol News, Vol. 46(5), p. 37 (1975), as representing "the superior test method for the future". The test results obtained with this method under conditions close to those of physiological dissolution and adsorption are at least as reliable and reproducible as those obtained with the standard methods, e.g. the rotating basket method.

Thus, a capsule containing a mixture of Rifampicin (150.0 mg), crystalline cellulose (Avicel ® PH 101; 29.0 mg) and magnesium stearate (1.0 mg), which contains the same ingredients as the mixture of example 4 of the above Japanese patent disclosure with only minor quantitative differences, shows the following dissolution rates in an acidic aqueous medium of pH 1.5 (containing per 1000 ml solution 2.0 g of sodium chloride and 2.92 g of hydrogen chloride, the latter corresponding to 80.08 ml 1-n. aqueous hydrochloric acid) and in a slightly basic aqueous medium of pH 7.50 (containing per 1000 ml solution 6.804 g of potassium dihydrogen phosphate and 1.636 g of sodium hydroxide), using the above described column method (laminar flow conditions with an average flow rate of about 16.0 ml/min. produced by a pulsation rate of 130 per minute; cell volume 20 ml; temperature of the medium: 37° C.):

| measurements (minutes) | medium pH 1.5[a] | | | | | | | | medium pH 7.5[b] | | | | | | | |
|---|---|---|---|---|---|---|---|---|---|---|---|---|---|---|---|---|
| Exp. | 1 | 2 | 3 | 4 | 5 | 6 | 7 | 8 | 1 | 2 | 3 | 4 | 5 | 6 | 7 | 8 |
| 10 | 35.5 | 18.6 | 20.2 | 21.3 | 8.3 | 35.0 | 16.1 | 30.3 | 5.4 | 5.5 | 16.4 | 16.4 | 12.8 | 2.1 | 7.1 | 13.9 |
| 20 | 89.0 | 67.4 | 79.1 | 89.4 | 62.7 | 86.1 | 70.6 | 76.1 | 15.6 | 37.6 | 32.0 | 36.6 | 34.4 | 11.4 | 18.6 | 30.0 |
| 30 | 101.5 | 97.8 | 98.7 | 102.5 | 100.6 | 99.6 | 95.6 | 96.7 | 23.3 | 69.3 | 42.9 | 48.9 | 51.5 | 19.0 | 27.3 | 46.8 |
| 40 | 102.4 | 100.9 | 104.7 | 103.0 | 103.5 | 100.0 | 97.6 | 98.3 | 30.8 | 82.9 | 51.2 | 58.8 | 65.5 | 24.5 | 34.7 | 57.7 |
| 50 | 102.8 | 101.3 | 105.0 | 103.0 | 103.9 | 100.1 | 97.8 | 98.5 | 38.4 | 88.9 | 59.0 | 65.7 | 70.6 | 29.4 | 40.3 | 64.3 |

-continued

| measurements | medium pH 1.5[a] | | | | | | | | medium pH 7.5[b] | | | | | | | |
|---|---|---|---|---|---|---|---|---|---|---|---|---|---|---|---|---|
| | Exp. | | | | | | | | | | | | | | | |
| (minutes) | 1 | 2 | 3 | 4 | 5 | 6 | 7 | 8 | 1 | 2 | 3 | 4 | 5 | 6 | 7 | 8 |
| 60 | 103.2 | 101.6 | 105.1 | 103.0 | 103.9 | 100.1 | 97.8 | 98.5 | 44.5 | 92.0 | 65.1 | 70.6 | 85.7 | 33.2 | 45.3 | 69.8 |

[a] flow rate Exp. 1: 16.0 ml/min.; 2: 15.9 ml/min.; 3: 15.9 ml/min.; 4: 15.9 ml/min.; 5: 16.0 ml/min.; 6: 15.9 ml/min.; 7: 16.0 ml/min.; 8: 16.1 ml/min
[b] flow rate Exp. 1: 16.0 ml/min.; 2: 16.1 ml/min.; 3: 15.9 ml/min.; 4. 15,9 ml/min.; 5: 16.0 ml/min.; 6: 15.9 ml/min.; 7: 16.0 ml/min.; 8: 16.1 ml/min.;

These data show, that the dissolution properties of Rifampicin capsules of the type described in example 4 of the description of the Japan patent disclosure No. Sho 53-133624 in the neutral to slightly basic medium are erratic; in three experiments, the dissolution after 1 hour remains below 50%. It has also been found that a preparation with an in vitro release of <60% in one hour would give an insufficient blood level value in vivo (one experiment below 35%). In order to guarantee a consistently uniform release of the active ingredient Rifampicin from a solid pharmaceutical preparation for oral administration, this type of composition is, therefore, not satisfactory and obviously needs improvement.

It has now been found, that when sodium lauryl sulfate is added to a mixture of Rifampicin and crystalline cellulose, containing a lubricant ingredient, solid pharmaceutical preparations can be obtained, which show consistently uniform dissolution rates. Thus, the dissolution rates of capsules containing a mixture of Rifampicin (150.0 mg), crystalline cellulose (Avicel ® PH 101; 25.5 mg), sodium lauryl sulfate (Duponol ® C; 1.5 mg) and magnesium stearate (3.0 mg), when measured according to the above described column method, using the same acidic (pH 1.5) and slightly basic (pH 7.5) media, are consistently more uniform and more complete, than those of the compositions disclosed in the Japanese Patent disclosure No. 53-133624:

practical purposes a complete availability of the active ingredient.

The present invention, therefore, has for its object a novel solid pharmaceutical composition containing a mixture of from about 75% to about 90% of Rifampicin, of from about 5% to about 20% of crystalline cellulose, of from about 0.5% to about 5% of sodium lauryl sulfate and of from about 0.5% to about 5% of a pharmaceutically acceptable lubricant.

More particularly, the present invention has for its object a new solid pharmaceutical composition containing a mixture of from about 80% to about 85% of Rifampicin, of from about 10% to about 20% of crystalline cellulose, of from about 0,5% to about 2% of sodium lauryl sulfate and of from about 1% to about 4% of a pharmaceutically acceptable lubricant.

The solid pharmaceutical composition is primarily useful for the oral administration and can be in the form of an uncoated or coated tablet, but is advantageously a capsule. The latter is primarily a hard gelatine capsule, which may optionally be colored, for example, for identification purposes, with organic dyes or more advantageously with inorganic pigments, such as metal oxides, for example, iron oxides, e.g. red iron oxide, yellow iron oxide, brown iron oxide or black iron oxide and/or titanium oxide.

The active ingredient, Rifampicin, can be used in the

| measurements | medium pH 1.5[c] | | | | | | | | | medium pH 7.5[d] | | | | | | | |
|---|---|---|---|---|---|---|---|---|---|---|---|---|---|---|---|---|---|
| | Exp. | | | | | | | | | | | | | | | | |
| (minutes) | 1 | 2 | 3 | 4 | 5 | 6 | 7 | 8 | 9 | 1 | 2 | 3 | 4 | 5 | 6 | 7 | 8 |
| 10 | 48.3 | 44.1 | 24.0 | 24.7 | 31.3 | 46.2 | 33.2 | 26.6 | 14.6 | 45.5 | 46.1 | 39.5 | 46.8 | 39.9 | 41.7 | 43.1 | 39.4 |
| 20 | 93.8 | 89.1 | 66.2 | 67.6 | 83.5 | 85.3 | 68.6 | 60.6 | 53.0 | 64.2 | 64.9 | 54.9 | 72.8 | 68.0 | 68.4 | 71.9 | 71.5 |
| 30 | 103.1 | 101.2 | 92.2 | 93.2 | 98.4 | 100.2 | 85.9 | 79.9 | 77.6 | 75.2 | 76.5 | 64.9 | 86.8 | 84.8 | 83.2 | 86.8 | 87.6 |
| 40 | 104.6 | 104.3 | 101.5 | 100.3 | 100.9 | 103.3 | 94.5 | 91.7 | 90.5 | 81.8 | 84.1 | 71.8 | 94.4 | 93.8 | 91.2 | 94.6 | 95.6 |
| 50 | 105.1 | 106.3 | 105.3 | 100.9 | 101.1 | 103.6 | 98.1 | 97.5 | 96.9 | 87.7 | 88.9 | 76.7 | 98.5 | 98.7 | 95.7 | 98.8 | 99.7 |
| 60 | 105.2 | 106.9 | 107.95 | 101.0 | 101.2 | 103.8 | 99.4 | 99.3 | 99.5 | 91.0 | 91.8 | 79.5 | 100.7 | 101.4 | 98.1 | 100.9 | 101.5 |

[c] flow rate Exp. 1: 16.0 ml/min.; 2: 15.9 ml/min.; 3: 16.1 ml/min.; 4.–9.: 15.9 ml/min.
[d] flow rate Exp. 1: 15.8 ml/min.; 2: 15.7 ml/min.; 3: 15.8 ml/min.; 4.–6.: 15.9 ml/min.; 7: 16.0 ml/min.; 8: 15.9 ml/min.

The data show, that capsules, which contain a mixture of the active ingredient and the auxiliary substances according to the present invention, have dissolution rates, which are consistently uniform and complete in both, the acidic medium simulating the conditions of the normal and healthy human stomach and the neutral to slightly basic medium simulating abnormal human stomach conditions, as well as those of the lower gastro-intestinal tract. The fact, that the release of Rifampicin from the pharmaceutical preparations must be consistent, is of importance, in case the latter is removed from the acidic stomach into the slightly basic lower intestinal tract, before all of the active ingredient has been eluted from the preparation and made available to the body. In other words, the solid Rifampicin preparations of the present invention show dissolution rates, which are virtually independent of the surrounding pH conditions and guarantee a consistently uniform and for all usual cystalline form as specified, for example, in US Pharmacopeia, Vol. 80, p. 710 (1980); Mack Printing Co., Easton (PA) USA). The average particle size is about 100 $\mu$m, at least 50% of the particle size is greater than 40 $\mu$m and at most 1% is greater than 500 $\mu$m.

The crystalline cellulose present in the mixture for the pharmaceutical preparations of this invention is preferably used in microcrystalline form. Usually, it is manufactured from purified $\alpha$-cellulose by mechanical and, in certain instances, by chemical (acidic hydrolysis) treatment. It contains about 5% water and decomposes at about 260° to 270° C., and its particle size is between about 1 $\mu$m and about 250 $\mu$m and advantageously between about 20 $\mu$m and 100 $\mu$m, an average particle size of about 50 $\mu$m being preferred.

Sodium lauryl sulfate represents a mixture of sodium higher alkyl sulfates, which consists mainly of the sodium n-dodecyl sulfate. It is prepared, for example, from dodecylalcohol by treatment with sulfuric acid at about 20° to 30° C. or with chlorosulfonic acid. The use of this auxiliary ingredient in a mixture of Rifampicin and microcrystalline cellulose, containing a lubricant, causes, as has been shown above, a surprising improvement of the dissolution properties of solid pharmaceutical preparations consisting of such mixtures. This despite the fact, that in the Japanese patent disclosure No. Sho 53-133624 the addition of sodium lauryl sulfate as a conventional elution improver to solid pharmaceutical preparations containing Rifampicin has been described as being ineffective. Thus, the elution properties of a mixture of Rifampicin (150 mg), sodium lauryl sulfate (30 mg) and calcium stearate (5 mg) shows a very low dissolution rate, even after 120 minutes (FIG. 2), when determined with the rotating basket method, using an acidic medium with a pH-value of 3. It is, therefore, suprising, that the addition of sodium lauryl sulfate to the mixture of Rifampicin and crystalline cellulose, contaning a lubricant (a mixture which is described in example 4 of the above Japanese patent disclosure), instead of having the expected negative effect on the dissolution rate of the preparation, causes a clear-cut improvement, particularly under neutral to slightly basic conditions.

The usual pharmaceutically acceptable lubricants can be used in the solid pharmaceutical preparations of the present invention; primarily alkaline or particularly alkaline earth metal salts of higher alkanoic acids, such as magnesium stearate or calcium stearate, are being used, whereby ingredients of standard quality and acceptability are preferred.

The solid pharmaceutical compositions of this invention are prepared according to known methods, usually by mixing the ingredients, whereby the latter may be added simultaneously or subsequently; the mixing may be interrupted and/or followed by a sieving procedure prior to the manufacture of the final solid form. The latter may be achieved, for example, by filling the mixture into capsules or compressing it into tablets.

The following examples illustrate the present invention, but are not intended to limit its scope.

EXAMPLE 1

Capsules, containing 150 mg of Rifampicin, are prepared as follows:

| Ingredients (for 8'000 capsules) | |
|---|---|
| Rifampicin | 1.200 kg |
| microcrystalline cellulose (Avicel ® PH 101) | 0.204 kg |
| sodium lauryl sulfate (Duponol ® C) | 0.012 kg |
| magnesium stearate | 0.024 kg |

The sodium lauryl sulfate is sieved through a sieve having a mesh width of about 0.2 mm and added to the Rifampicin and mixed during 10 minutes. The microcrystalline cellulose is sieved through a sieve with a mesh width of about 0.9 mm and added to the mixture; mixing is continued during 10 minutes. The magnesium stearate is sieved through a sieve with a mesh width of about 0.8 mm and added to the mixture, which is mixed for additional 3 minutes. The resulting mixture is filled into No. 2 hard gelatine capsules.

EXAMPLE 2

Capsules containing 150 mg of Rifampicin are prepared as follows:

| Ingredients (for 20'000 capsules) | |
|---|---|
| Rifampicin | 3.000 kg |
| microcrystalline cellulose (Avicel ® PH 101) | 0.500 kg |
| sodium lauryl sulfate (Duponol ® C) | 0.040 kg |
| magnesium stearate | 0.060 kg |

The mixture is prepared as described in example 1 and filled into No. 2 hard gelatine capsules.

We claim:

1. A solid pharmaceutical composition consisting essentially of a mixture of from about 75% to about 90% of rifampicin, of from about 5% to about 20% of crystalline cellulose, of from about 0.5% to about 5% of sodium lauryl sulfate, and of from about 0.5% to about 5% of magnesium stearate, said solid pharmaceutical composition being in the form of a capsule suitable for oral administration.

2. A solid pharmaceutical composition according to claim 1 consisting essentially of a mixture of from about 80% to about 85% of Rifampicin, of from about 10% to about 20% of crystalline cellulose, of from about 0.5% to about 2% of sodium lauryl sulfate and of from about 1% to about 4% of magnesium stearate.

3. A solid pharmaceutical composition according to claim 1, wherein the crystalline cellulose is in microcrystalline form.

4. A method of antibiotic treatment of a mammal comprising administering an antibiotically effective amount of a composition of claim 1 to said mammal.

* * * * *